US00PP29365P3

(12) United States Plant Patent
Corder et al.

(10) Patent No.: US PP29,365 P3
(45) Date of Patent: Jun. 12, 2018

(54) APPLE TREE NAMED 'BIGBUCKS'

(50) Latin Name: ***Malus domestica* Borkh.**
Varietal Denomination: BIGBUCKS

(71) Applicant: Pink Vein (Pty) Ltd., Elgin, Western Cape (ZA)

(72) Inventors: Derek Alexander Corder, Elgin (ZA); Peter John Nel, Somerset West (ZA); Anthony George Rawbone-Viljoen, Elgin (ZA)

(73) Assignee: Pink Vein (Pty) Ltd., Elgin, Western Cape (ZA)

( * ) Notice: Subject to any disclaimer, the term of this patent is extended or adjusted under 35 U.S.C. 154(b) by 37 days.

(21) Appl. No.: 14/999,781

(22) Filed: Jun. 27, 2016

(65) Prior Publication Data

US 2017/0374775 P1 Dec. 28, 2017

(51) Int. Cl.
*A01H 5/08* (2018.01)

(52) U.S. Cl.
USPC ..... Plt./162
CPC ..... *A01H 5/0875* (2013.01)

(58) Field of Classification Search
USPC ..... Plt./161, 162
CPC ..... A01H 5/0875
See application file for complete search history.

(56) References Cited

PUBLICATIONS

GTITM UPOVROM Plant Variety Database Citation for 'BigBucks' as per ZA PBR PT6281; Mar. 11, 2011; 1 page.*
Printout of application information from PLUTO Plant Variety Database for corresponding South African application No. Pt 6281 filed Mar. 11, 2011 (1 page) (http://www.wipo.int/pluto).

* cited by examiner

*Primary Examiner* — Kent L Bell
(74) *Attorney, Agent, or Firm* — Foley & Lardner LLP

(57) ABSTRACT

'BIGBUCKS' is a new and distinct variety of Gala apple, selected for its dark red over color on 90-100% of the fruit skin surface with a full blush. It is distinguished from its parent variety 'Royal Gala' (U.S. Plant Pat. No. 4,121) and other Gala varieties by its unique dark red full blush over color, red coloration of the stalk, and red coloration of the main vein on the lower side of the leaf.

6 Drawing Sheets

Latin name of the genus and species of the plant claimed: *Malus domestica* Borkh.

Variety denomination: 'BIGBUCKS'.

BACKGROUND OF THE INVENTION

The present invention relates to a new and distinct variety of Apple tree, botanically known as *Malus domestica* Borkh. of the Rosaceae family, and hereinafter referred to by the variety denomination 'BIGBUCKS'.

The new *Malus* variety was discovered as a naturally-occurring whole-tree mutation of 'Royal Gala' (U.S. Plant Pat. No. 4,121) growing in a cultivated orchard in 2011 in Elgin, South Africa, (GPS 34.154915° S ,19.045706° E). The orchard where the variety was discovered is northern facing and the soil type is loamy soil with 700 cold units in Elgin, South Africa. The conditions closely approximate the characteristics for apple cultivating used in commercial practice.

The new *Malus* variety was selected by the inventors based on its dark red blush over color, which appears as a solid flush, and which distinguishes the new variety from the parent variety 'Royal Gala' (U.S. Plant Pat. No. 4,121), where the over color is medium red and the pattern is striped.

The variety was asexually reproduced by grafting onto MM109 rootstock in February 2012 in Riviersonderend, South Africa (GPS 34.144002° S, 19.906522° E). The variety was planted in a larger commercial planting in 2013 for further observation. 'BIGBUCKS' has demonstrated that the combination of characteristics as herein disclosed are firmly fixed and retained through successive generations of asexual reproduction. 'BIGBUCKS' has been observed to remain true to type over successive asexually propagated generations.

BRIEF DESCRIPTION OF THE INVENTION

The following traits have been repeatedly observed and are determined to be unique characteristics of 'BIGBUCKS' which in combination distinguish this variety as new and distinct:

1. Dark red solid flushed over color on 90-100% of fruit skin surface;
2. Distinct red coloration of the main vein on the lower side of the mature leaf at harvest time;
3. Dark red coloration of the fruit stalk ; and
4. Intense red coloration at the flower filament base.

Of the many commercial varieties known to the present inventor(s), the most similar in comparison to the new *Malus* variety 'BIGBUCKS' is the *Malus* variety 'Royal Beaut' (unpatented), in the following characteristics described in Table 1:

TABLE 1

| Characteristic | New Variety 'BIGBUCKS'. | Comparison Variety 'Royal Beaut' (unpatented). |
|---|---|---|
| Over color and pattern | Dark red with only solid flush pattern. | Medium red with solid flush and weakly striped pattern. |
| Color of the leaf main vein on lower side. | Red. | Green. |
| Color of Fruit stalk | Dark red. | Green. |
| Color of Base of Flower Filament | Red. | Pale Green. |

BRIEF DESCRIPTION OF THE PHOTOGRAPHS

The accompanying photographs, in combination with the brief description given, illustrate the overall appearance of the new *Malus* variety 'BIGBUCKS' showing the colors as true as is reasonably possible with colored reproductions of this type.

Colors in the photographs may differ slightly from the color values cited in the detailed botanical description, which accurately describe the color of 'BIGBUCKS'.

DETAILED BOTANICAL DESCRIPTION

Figure 1:
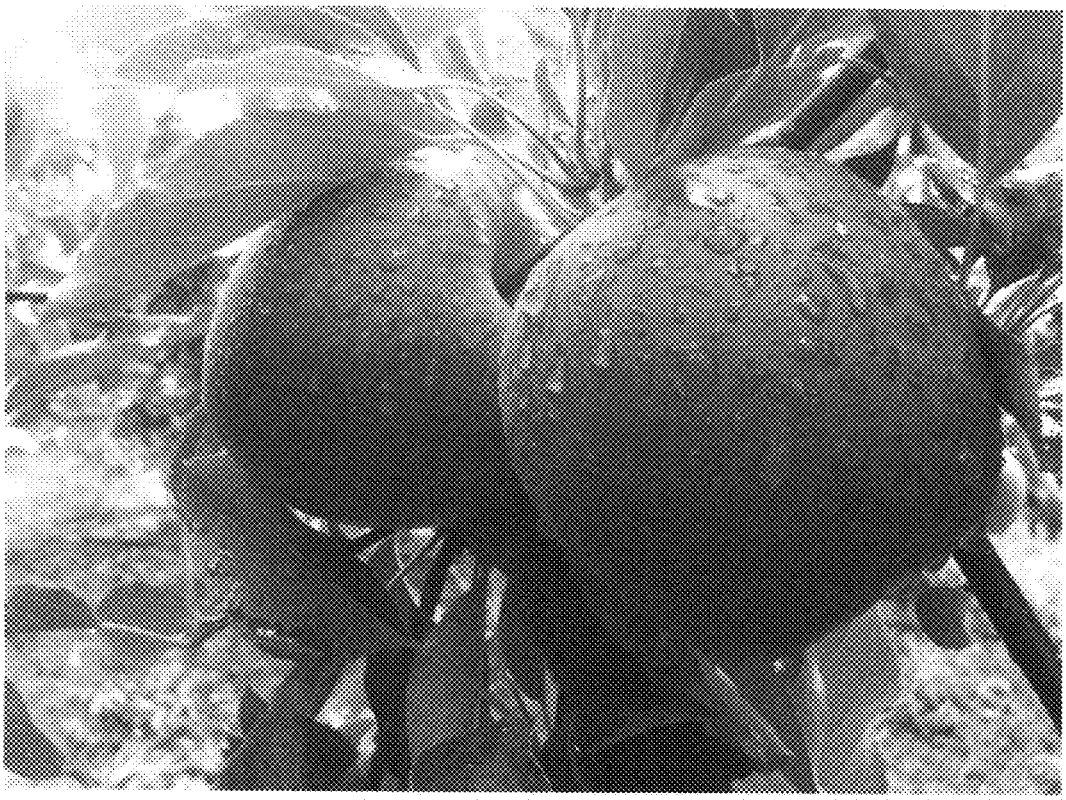
FIG. 1 shows a typical fruit of 'BIGBUCKS' at harvest time.
Figure 2:
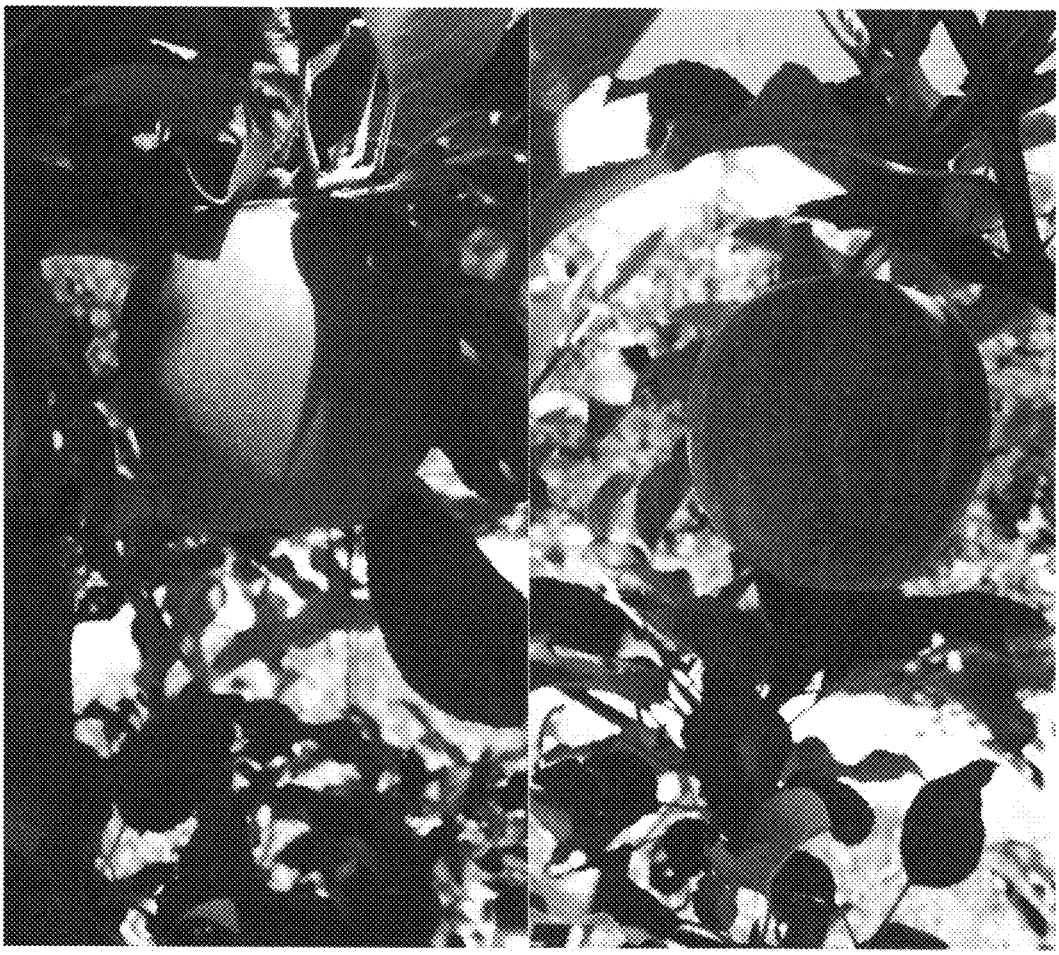
FIG. 2 shows a typical fruit of 'BIGBUCKS' 14 days before harvest time (left), compared with a typical fruit of 'Royal Beaut' (unpatented) 14 days before harvest time (right).
Figure 3:
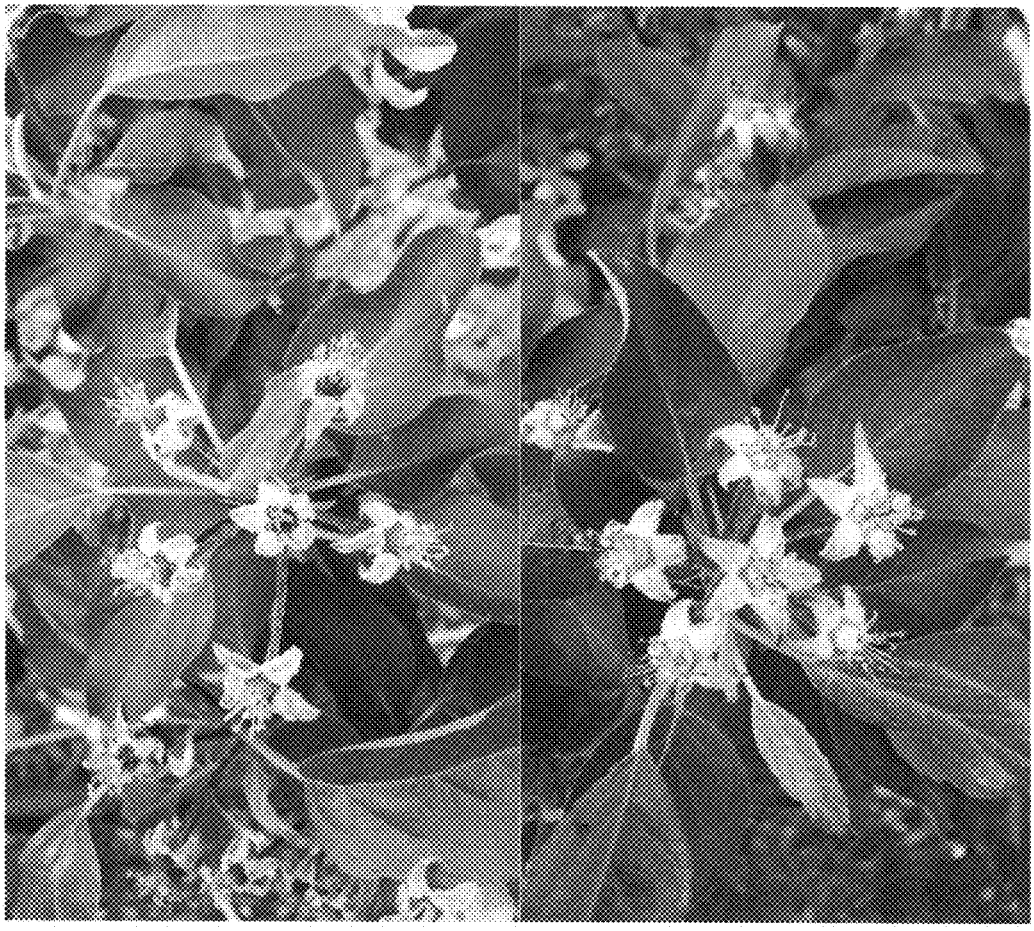
FIG. 3 shows the base of the filament of the flower of 'BIGBUCKS' (left), compared with the base of the filament of the flower of 'Royal Beaut' (unpatented) (right).
Figure 4:
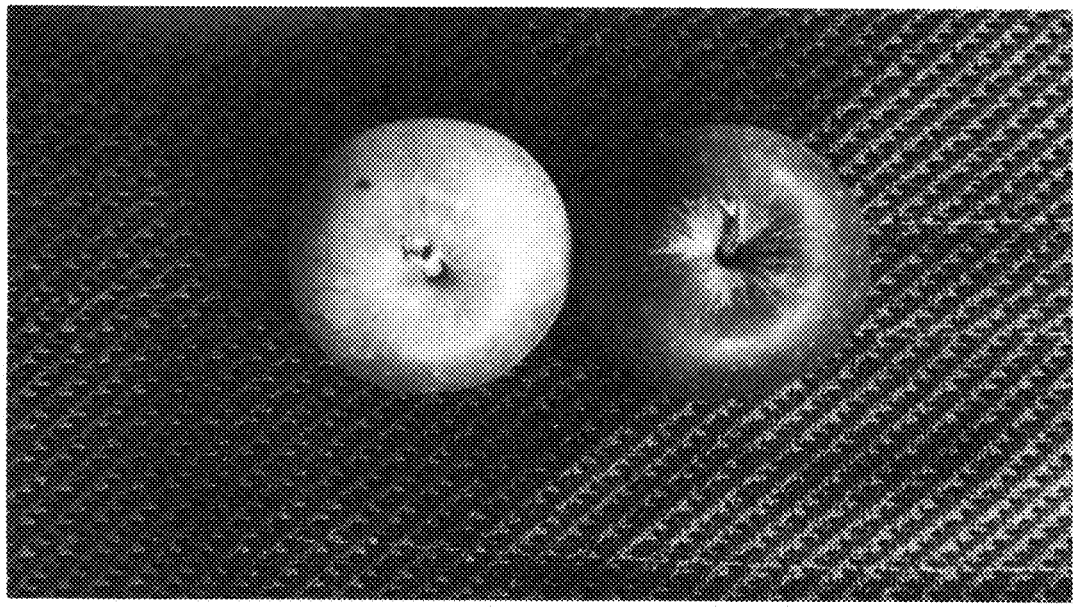
FIG. 4 shows a typical whole fruit 30 days before harvest of 'BIGBUCKS' (right), showing a dark red stalk, compared with a typical whole fruit of 'Royal Beaut' (unpatented) (left), showing a green stalk.
Figure 5:
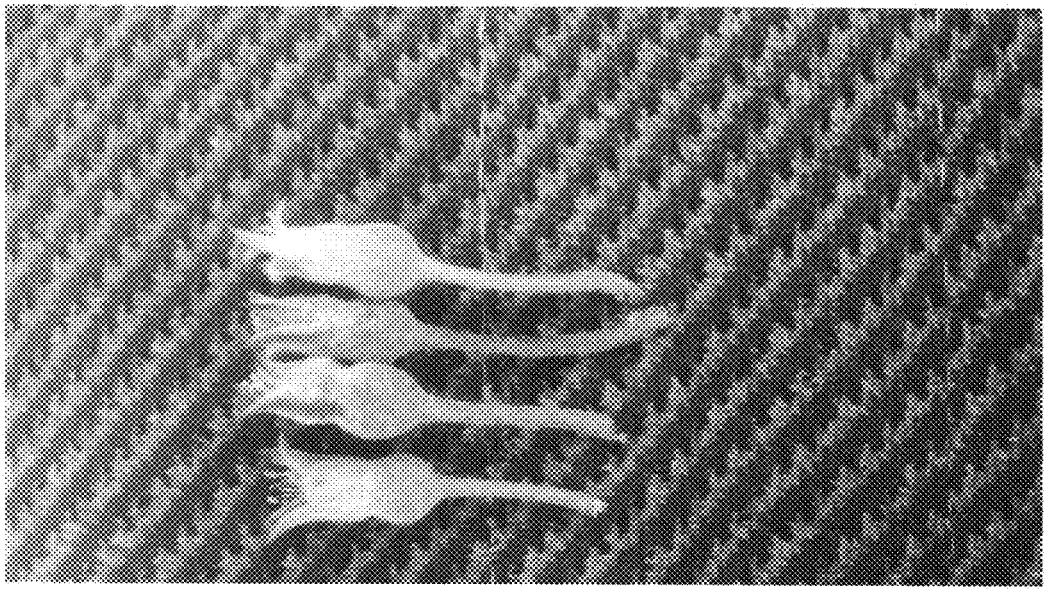
FIG. 5 shows the difference in color of the fruitlet (7 mm) of 'Royal Beaut' (unpatented) (top), and 'BIGBUCKS' (bottom).
Figure 6:
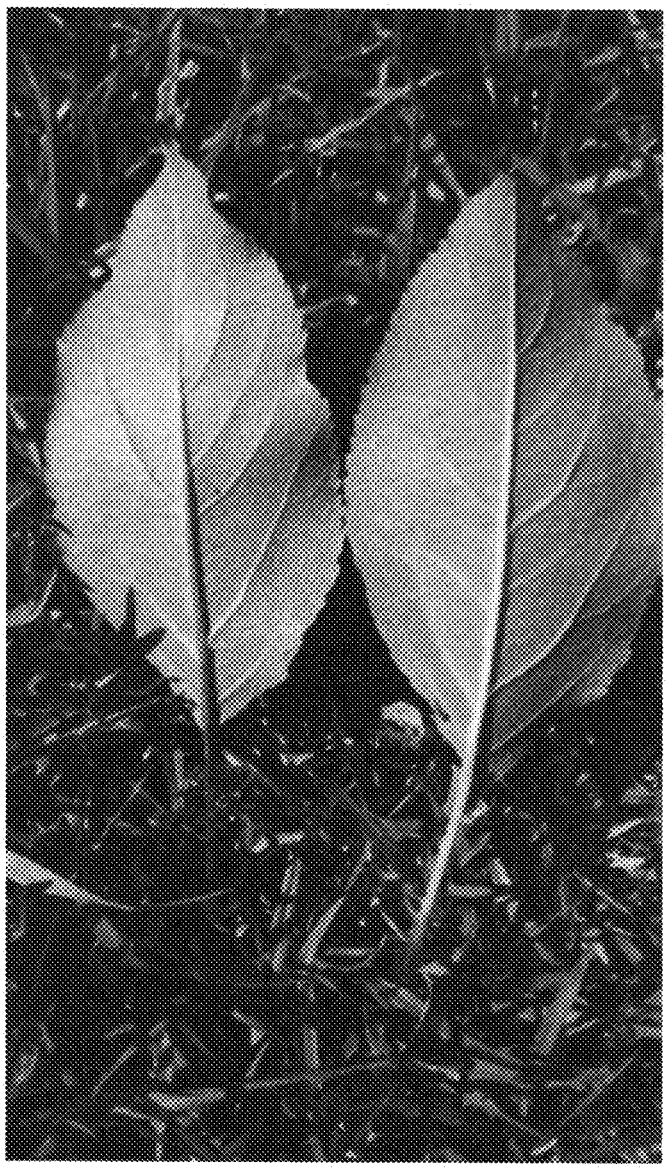
FIG. 6 shows the difference in color of the main vein on the lower side of a typical leaf of 'BIGBUCKS' (left), and 'Royal Beaut' (unpatented) (right).

The new *Malus* variety 'BIGBUCKS' has not been observed under all possible environmental conditions. The phenotype of the new variety may vary with variations in environment such as temperature, light intensity, and day length without any change in the genotype of the Apple tree.

Unless otherwise stated, the detailed botanical description includes observations, measurements and values based on 3 year old 'BIGBUCKS' trees grown in the Apple farm in Elgin, South Africa. The aforementioned photographs, together with the following observations, measurements and values describe trees of 'BIGBUCKS' as grown in Elgin, South Africa.

Quantified measurements are expressed as an average of measurements taken from a number of trees of 'BIGBUCKS'. The measurements of any individual tree or any group of trees, of the new variety may vary from the stated average.

All colors are described according to The Royal Horticultural Society Color Chart (R.H.S.), (Fifth Edition), except where general colors of ordinary significance are used.

All of the trees of 'BIGBUCKS', insofar as they have been observed, have been identical in all the characteristics described below.

Classification:

*Botanical.*—*Malus domestica* Borkh.

Parentage: A naturally-occurring whole-tree mutation of 'Royal Gala' (U.S. Plant Pat. No. 4,121) in Elgin, South Africa.

Propagation: Chip budding.

Growing conditions:

*Light intensities.*—Full sunlight or slight shade.

*Temperature.*—During day, grown in range of 5° C. to 33° C.

*Fertilization.*—Standard for 'Royal Gala' (U.S. Plant Pat. No. 4,121).

*Growth regulators.*—None used.

*Pruning or trimming requirements.*—Standard for 3 year old 'Royal Gala' (U.S. Plant Pat. No. 4,121).

Tree:

*Age.*—Observed trees were 4 years old bearing trees.

*Vigor.*—Strong vigor; (similar to 'Royal Gala' (U.S. Plant Pat. No. 4,121).

*Form.*—Ramified.

*Habit.*—A semi-upright tree with one trunk and 1 leader; main branches spreading; crown symmetrical.

*Size at maturity.*—Height: about 3 m. Spread: about 1.5 m.

Branch:

*Number per tree.*—About 12.

*Crotch angle.*—45 degrees to 90 degrees.

*Length.*—730 mm.

*Diameter.*—21 mm.

*Texture.*—Smooth.

*Bark color.*—Grayed-white 156 C.

*Branch lenticels.*—1 mm in diameter, round, color Grayed-white 156B and the number is 4-6 per $cm^2$.

Trunk:

*Height* (*up to leaders*).—900 mm.

*Diameter.*—83 mm.

*Texture.*—At first, smooth with numerous lenticels, then shallow furrows and scaly ridges.

*Bark color.*—Grey-green 198C.

*Lenticels.*—4 mm-7 mm in length, 1 mm in width, color Grayed-brown 199B. Number per $cm^2$ is 3.

One year old shoot:

*Internode length.*—26 mm.

*Thickness.*—5 mm.

*Color.*—Grey-purple 183B.

*Pubescence.*—Moderate at distal half of shoot (same as 'Royal Gala' (U.S. Plant Pat. No. 4,121)).

*Lenticels.*—0.6 mm in diameter, round, color Orange-white 159B and the number is 10-13 per $cm^2$.

Spurs:

*Shape.*—Short conical.

*Length.*—12-14 mm.

*Color.*—Brown 200C.

*Distance between each spur.*—About 30 mm.

*Diameter.*—About 5 mm.

*Number of fruit per spur.*—About 2-4.

Leaves:
*Arrangement*.—Alternate, simple, petiolated.
*Length*.—Medium (90 mm).
*Width*.—Very narrow (47 mm).
*Shape*.—Narrow Elliptic.
*Base shape*.—Truncate.
*Apex shape*.—Right Angled.
*Margin*.—Serrate.
*Texture upper surface*.—Smooth.
*Pubescence*.—Upper surface: Absent or very weak. Lower surface: Weak.
*Attitude in relation to shoot*.—Upwards.
*Color*.—Upper surface: Green, N137C. Lower surface: Green 148B.
*Main vein*.—Color of upper side of leaf: Yellow green 144B. Color on lower side of leaf: Red 59A.

Petiole:
*Length*.—31 mm.
*Diameter*.—1.9 mm.
*Color*.—Red N77A.
*Texture*.—Smooth.

Stipule:
*Arrangement*.—At base of petiole.
*Length*.—9 mm.
*Width*.—2 mm.
*Shape*.—Narrow elliptic.
*Color on upper side*.—Green 147B.
*Color on lower side*.—Green 147 B.

Inflorescence:
*Blooming time*.—Full bloom on about 15 October in Southern Hemisphere.
*Blooming period*.—About 10 October to 29 October in Southern Hemisphere.
*Fragrance*.—Weak.
*Number of flowers per inflorescence*.—6.
*Flower*.—Corolla diameter: 44 mm. Flower depth: 12 mm.

Petals:
*Arrangement*.—Free.
*Number per flower*.—Five.
*Overall shape*.—Narrow elliptic.
*Apex shape*.—Moderately obtuse.
*Base shape*.—Acute.
*Texture* (*upper and lower surface*).—Smooth.
*Margin*.—Entire, cupped.
*Color of upper surface*.—White 155D with tinges of Red 59C.
*Color of lower surface*.—White 155D with tinges of Red 59C.

Sepals:
*Number per flower*.—Five.
*Shape*.—Pointed to wedged shape.
*Color*.—Yellow Green 145D.
*Margin*.—Entire.
*Length*.—4 mm.
*Width*.—4 mm.

Pedicel:
*Color*.—Yellow-green 144D.
*Length*.—26 mm.
*Width*.—2 mm.
*Texture*.—Smooth.

Pistils:
*Pistil number*.—5.
*Stigma*.—Length: 1 mm, color: Yellow-green 144B.
*Style*.—Length: 3 mm, width: 1 mm, color: Yellow-green 144B.
*Ovary*.—Length: 4 mm, width: 1.5 mm, color: Yellow-green 143C.

Stamen:
*Anther color*.—Yellow 11D.
*Length*.—9 mm.
*Width*.—0.3 mm.
*Pollen amount*.—Abundant.
*Pollen color*.—Yellow 11D.
*Filament*.—White 159 B.
*Color at base of filament* (*after petal drop*).—Red 59A.

Fruit:
*Maturity when described*.—Ripe for eating first week of February in Southern Hemisphere.
*Production*.—About 5000 Kg per Hectare.
*Maturity period after full bloom*.—About 100 days after full bloom.
*Date of first and last picking* (*harvest*).—February 1 to February 15 in Elgin, South Africa (GPS 34.15432° S, 19.047473° E).
*General shape*.—Cylindrical-globose.
*Average weight*.—145 g.
*Fruit size*.—Height: 65.2 mm. Diameter (at widest point): 71 mm.
*Position of maximum diameter*.—Middle (½ of height).
*Stalk*.—Length: 28 mm. Diameter: 2 mm. Color: Red 59B.
*Stalk cavity*.—Depth: 15 mm. Width: 32 mm.
*Eye basin*.—Depth: 7.6 mm. Width: 32.3 mm.
*Crowning at calyx end*.—Moderate.
*Position of sepals*.—Partly open.
*Calyx tube*.—Funnel form.
*Skin*.—Thickness: 0.1 mm. Bloom: Weak. Greasiness: Absent. Firmness (at picking time): 7 to 9 kg/cm$^2$. Ground color: Not visible. Color of the over color: Red 53A. Percentage of skin surface with over color: 90 to 100%. Pattern of over color: Solid flush. Intensity of over color: Dark.
*Flesh*.—Color: Cream yellow 12C. Texture: Crisp and juicy. Sugar content (at picking time): 13° Brix. Acidity/Starch (at picking time) Starch conversion 30%.
*Core*.—Symmetry of core: Symmetrical. Distinctness of core lines: Medium.
*Locules*.—Number (per fruit): 5. Length: 23 mm. Width: 22 mm. Form: Moderately open.

Seed:
*Number per fruit*.—8.
*Number per locule*.—1-2.
*Shape*.—Ovate.
*Length*.—7 mm.
*Width*.—4.5 mm.
*Texture*.—Smooth.
*Color*.—Grayed-Orange 177A.

Use: Fresh market.

Disease/pest resistance: No resistance to Apple Scab (*Venturia inaequalis*) observed (same as 'Royal Gala' (U.S. Plant Pat. No. 4,121)).

Disease/pest susceptibility: No abnormal susceptibility observed (same as 'Royal Gala' (U.S. Plant Pat. No. 4,121)).

Winter hardiness: No information available in Southern Hemisphere.

Drought/heat tolerance: Tolerant to temperatures up to 40° C., growth is limited by drought periods without irrigation.

Keeping quality: The fruit can be stored in cold temperature conditions for up to 6 months without losing firmness and juiciness. It has a shelf life up to 2 weeks without losing firmness and juiciness.

Shipping/storage characteristics: Not susceptible to bruising (same as 'Royal Gala' (U.S. Plant Pat. No. 4,121)).

I claim:

1. A new and distinct variety of *Malus domestica* Borkh. apple tree named 'BIGBUCKS', as illustrated and described herein.

* * * * *